(12) United States Patent
O'Keefe et al.

(10) Patent No.: US 8,432,287 B2
(45) Date of Patent: Apr. 30, 2013

(54) APPARATUS FOR CONTROLLING ROOM LIGHTING IN RESPONSE TO BED EXIT

(75) Inventors: Christopher R. O'Keefe, Batesville, IN (US); Charles A. Lachenbruch, Lakeway, TX (US); Timothy Joseph Receveur, Guilford, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 360 days.

(21) Appl. No.: 12/847,160

(22) Filed: Jul. 30, 2010

(65) Prior Publication Data

US 2012/0025991 A1  Feb. 2, 2012

(51) Int. Cl.
G08B 23/00 (2006.01)

(52) U.S. Cl.
USPC .............. 340/573.4; 340/573.1; 340/575; 340/573.7

(58) Field of Classification Search ........... 340/573.4, 340/573.1
See application file for complete search history.

(56) References Cited

U.S. PATENT DOCUMENTS

| | | |
|---|---|---|
| 3,325,799 A | 6/1967 | Farris |
| 3,504,540 A | 4/1970 | Pradko et al. |
| 3,760,794 A | 9/1973 | Basham |
| 3,826,145 A | 7/1974 | McFarland |
| 3,836,900 A | 9/1974 | Mansfield |
| 3,890,958 A | 6/1975 | Fister et al. |
| 3,898,981 A | 8/1975 | Basham |
| 3,926,177 A | 12/1975 | Hardway, Jr. et al. |
| RE28,754 E | 3/1976 | Cook et al. |
| 3,961,201 A | 6/1976 | Rosenthal |
| 3,991,414 A | 11/1976 | Moran |
| 3,991,746 A | 11/1976 | Hanna |
| 4,020,482 A | 4/1977 | Feldl |
| 4,051,522 A | 9/1977 | Healy et al. |
| 4,097,939 A | 7/1978 | Peck et al. |
| 4,172,216 A | 10/1979 | O'Shea |
| 4,175,263 A | 11/1979 | Triplett et al. |
| 4,179,692 A | 12/1979 | Vance |
| 4,195,287 A | 3/1980 | McCoy et al. |
| 4,228,426 A | 10/1980 | Roberts |
| 4,242,672 A | 12/1980 | Gault |
| 4,245,651 A | 1/1981 | Frost |
| 4,264,904 A | 4/1981 | McCoy et al. |
| 4,275,385 A | 6/1981 | White |
| 4,295,133 A | 10/1981 | Vance |
| 4,320,766 A | 3/1982 | Alihanka et al. |
| 4,426,884 A | 1/1984 | Polchaninoff |
| 4,484,043 A | 11/1984 | Musick et al. |

(Continued)

FOREIGN PATENT DOCUMENTS

| | | |
|---|---|---|
| EP | 0 860 803 A2 | 8/1998 |
| WO | 2008/051949 | 10/2008 |

OTHER PUBLICATIONS

"SideCome® Communication System Design and Application Manual" from Hill-Rom:, Jul. 2002, 52 pages.

(Continued)

*Primary Examiner* — Kerri McNally
(74) *Attorney, Agent, or Firm* — Barnes & Thornburg LLP

(57) ABSTRACT

A patient position-activated room device control apparatus coupled to a patient's bed controls a device associated with a patient's room in response to the patient changing position relative to the patient's bed.

23 Claims, 7 Drawing Sheets

U.S. PATENT DOCUMENTS

| | | | |
|---|---|---|---|
| 4,539,560 A | 9/1985 | Fleck et al. | |
| 4,565,910 A | 1/1986 | Musick et al. | |
| 4,592,104 A | 6/1986 | Foster et al. | |
| 4,601,356 A | 7/1986 | Muccillo, Jr. | |
| 4,633,237 A | 12/1986 | Tucknott et al. | |
| 4,638,307 A | 1/1987 | Swartout | |
| 4,669,136 A | 6/1987 | Waters et al. | |
| 4,700,180 A * | 10/1987 | Vance | 340/573.4 |
| 4,793,428 A | 12/1988 | Swersey | |
| 4,803,744 A | 2/1989 | Peck et al. | |
| 4,926,951 A | 5/1990 | Carruth et al. | |
| 4,934,468 A | 6/1990 | Koerber, Sr. et al. | |
| 4,953,244 A | 9/1990 | Koerber, Sr. et al. | |
| 4,974,692 A | 12/1990 | Carruth et al. | |
| 5,010,774 A | 4/1991 | Kikuo et al. | |
| 5,023,967 A | 6/1991 | Ferrand | |
| 5,060,174 A | 10/1991 | Gross | |
| 5,115,223 A | 5/1992 | Moody | |
| 5,117,521 A | 6/1992 | Foster et al. | |
| 5,138,729 A | 8/1992 | Ferrand | |
| 5,144,284 A | 9/1992 | Hammett | |
| 5,170,364 A | 12/1992 | Gross et al. | |
| 5,253,656 A | 10/1993 | Rincoe et al. | |
| 5,269,388 A | 12/1993 | Reichow et al. | |
| 5,276,432 A | 1/1994 | Travis | |
| 5,279,010 A | 1/1994 | Ferrand et al. | |
| 5,317,769 A | 6/1994 | Weismiller et al. | |
| 5,353,012 A | 10/1994 | Barham et al. | |
| 5,377,372 A | 1/1995 | Rudolf et al. | |
| 5,393,935 A | 2/1995 | Hasty et al. | |
| 5,410,297 A | 4/1995 | Joseph et al. | |
| 5,561,412 A | 10/1996 | Novak et al. | |
| 5,633,627 A | 5/1997 | Newham | |
| 5,640,145 A | 6/1997 | Newham | |
| 5,654,694 A | 8/1997 | Newham | |
| 5,699,038 A | 12/1997 | Ulrich et al. | |
| 5,715,548 A | 2/1998 | Weismiller et al. | |
| 5,771,511 A | 6/1998 | Kummer et al. | |
| 5,806,111 A | 9/1998 | Heimbrock et al. | |
| 5,808,552 A | 9/1998 | Wiley et al. | |
| 5,838,223 A | 11/1998 | Gallant et al. | |
| 5,878,452 A | 3/1999 | Brooke et al. | |
| 5,906,016 A | 5/1999 | Ferrand et al. | |
| 6,067,019 A | 5/2000 | Scott | |
| 6,078,261 A | 6/2000 | Davsko | |
| 6,147,592 A | 11/2000 | Ulrich et al. | |
| 6,163,903 A | 12/2000 | Weismiller et al. | |
| 6,208,250 B1 | 3/2001 | Dixon et al. | |
| 6,252,512 B1 | 6/2001 | Riley | |
| 6,279,183 B1 | 8/2001 | Kummer et al. | |
| 6,286,166 B1 | 9/2001 | Henley et al. | |
| 6,320,510 B2 | 11/2001 | Menkedick et al. | |
| 6,321,878 B1 | 11/2001 | Mobley et al. | |
| 6,336,235 B1 | 1/2002 | Ruehl | |
| 6,362,725 B1 | 3/2002 | Ulrich et al. | |
| 6,430,766 B1 | 8/2002 | Henley et al. | |
| 6,611,979 B2 | 9/2003 | Welling et al. | |
| 6,658,680 B2 | 12/2003 | Osborne et al. | |
| 6,691,346 B2 | 2/2004 | Osborne et al. | |
| 6,791,460 B2 | 9/2004 | Dixon et al. | |
| 6,819,254 B2 | 11/2004 | Riley | |
| 6,876,303 B2 | 4/2005 | Reeder et al. | |
| 6,880,189 B2 | 4/2005 | Welling et al. | |
| 6,897,780 B2 | 5/2005 | Ulrich et al. | |
| 6,957,461 B2 | 10/2005 | Osborne et al. | |
| 6,978,500 B2 | 12/2005 | Osborne et al. | |
| 7,017,208 B2 | 3/2006 | Weismiller et al. | |
| 7,155,317 B1 | 12/2006 | Tran | |
| 7,171,708 B2 | 2/2007 | Osborne et al. | |
| 7,237,287 B2 | 7/2007 | Weismiller et al. | |
| 7,242,308 B2 | 7/2007 | Ulrich et al. | |
| 7,253,366 B2 | 8/2007 | Bhai | |
| 7,296,312 B2 | 11/2007 | Menkedick et al. | |
| 7,315,535 B2 | 1/2008 | Schuman | |
| 7,319,386 B2 | 1/2008 | Collins, Jr. et al. | |
| 7,330,127 B2 | 2/2008 | Price et al. | |
| 7,437,787 B2 | 10/2008 | Bhai | |
| 7,443,302 B2 | 10/2008 | Reeder et al. | |
| 7,454,805 B2 | 11/2008 | Osborne et al. | |
| 7,480,951 B2 | 1/2009 | Weismiller et al. | |
| 7,506,390 B2 | 3/2009 | Dixon et al. | |
| 7,515,059 B2 | 4/2009 | Price et al. | |
| 7,520,006 B2 | 4/2009 | Menkedick et al. | |
| 7,533,429 B2 | 5/2009 | Menkedick et al. | |
| 7,538,659 B2 | 5/2009 | Ulrich et al. | |
| 7,557,718 B2 | 7/2009 | Petrosenko et al. | |
| 7,568,246 B2 | 8/2009 | Weismiller et al. | |
| 7,610,637 B2 | 11/2009 | Menkedick et al. | |
| 7,657,956 B2 | 2/2010 | Stacy et al. | |
| 7,669,263 B2 | 3/2010 | Menkedick et al. | |
| 7,676,866 B2 | 3/2010 | Toms et al. | |
| 7,679,520 B2 | 3/2010 | Zerhusen et al. | |
| 7,703,158 B2 | 4/2010 | Wilker, Jr. et al. | |
| 7,746,218 B2 | 6/2010 | Collins, Jr. et al. | |
| 8,009,042 B2 * | 8/2011 | Steiner et al. | 340/541 |
| 2004/0257237 A1 * | 12/2004 | Bialecki et al. | 340/686.1 |
| 2007/0163045 A1 | 7/2007 | Becker et al. | |
| 2008/0169931 A1 | 7/2008 | Gentry et al. | |
| 2008/0205311 A1 | 8/2008 | Perkins et al. | |
| 2009/0302782 A1 | 12/2009 | Smith | |
| 2009/0313758 A1 | 12/2009 | Menkedick et al. | |
| 2010/0052917 A1 | 3/2010 | Sullivan et al. | |
| 2011/0102181 A1 * | 5/2011 | Metz et al. | 340/575 |

OTHER PUBLICATIONS

Advance Series Bed Services Manual (man026re) "4.37 Head Screw Assembly Chapter 4: Removal, Replacement, and Adjustment Procedures", Sep. 1998, pp. 89-106.

Advance Series Bed Services Manual (man026re) "Head Drive Unit Assembly—P/N 43353, 6200401 and 6200402; Chapter 5: Parts List ", Sep. 1998, pp. 150-160.

U.S. Appl. No. 12/912,320, filed Oct. 26, 2010, 36 pages.

U.S. Appl. No. 12/912,330, filed Oct. 26, 2010, 47 pages.

* cited by examiner

APPARATUS FOR CONTROLLING ROOM LIGHTING IN RESPONSE TO BED EXIT

BACKGROUND

This disclosure relates generally to patient beds and patient monitoring systems. More particularly, this disclosure relates to systems in which lighting in a patient's room is automatically controlled in response to a patient exiting the patient's bed.

Patient beds, such as those commonly found in healthcare facilities and other locations in which health care is provided, can have a number of features, including one or more features that are electronically controlled. Some examples of patient beds are the TotalCare® Bed System, the VersaCare® bed, the Advanta™ bed, and the Affinity® birthing bed, all of which are available from the Hill-Rom Company, Inc.

Bed exit systems, and other patient position monitoring systems, monitor a patient's position relative to a bed and issue alerts if the patient's position has changed or if the patient has moved to a position that may require the caregiver's attention. For example, if the patient has exited the bed, the patient position monitoring system may issue an audible or visual alarm. Some patient beds, such as the TotalCare® bed, the VersaCare® bed, and the Advanta™ bed, have a bed exit or patient position monitoring system incorporated therein. Some examples of patient beds that have a patient position monitoring feature are disclosed in U.S. Pat. Nos. 7,515,059; 7,538,659; 7,557,718; 7,568,246; 7,657,956 and 7,679,520. Other patient position monitoring systems may be sold as separate devices that can be used in connection with a bed.

Some patient beds can be connected to a healthcare facility's healthcare communication system (e.g., a nurse call system) to send data generated at the bed to the healthcare communication system. For example, if a patient has exited the bed, the bed may send a bed exit signal to the nurse call system, and the nurse call system may send a notification to a output device that is connected to the nurse call system (such as a dome light, a nurse's station, a speaker, or a caregiver's mobile communication device). Some examples of systems in which beds may communicate data to a nurse call system or hospital communication system are disclosed in U.S. Pat. Nos. 7,319,386; 6,362,725; and 5,699,038.

SUMMARY

The present invention comprises one or more of the features recited in the appended claims and/or the following features which, alone or in any combination, may comprise patentable subject matter.

According to one aspect of this disclosure, a bed system includes a bed, and a bed exit monitor coupled to the bed. The bed exit monitor detects a patient exiting the bed. The bed system also includes a controller that is coupled to the bed exit monitor and to lighting, which may be coupled to the bed or spaced from the bed. The lighting illuminates at least a portion of a room in response to being turned on. The lighting is configured to be turned on by a manually operated switch. The controller is configured to receive a first signal from the bed exit monitor and use the first signal to control the turning on of the lighting independently of the manually operated switch.

The bed system may include a detector coupled to the controller. The detector may be configured to determine whether the lighting has been turned on or off via the manually operated switch. The controller may be configured to receive a status signal from the detector, where the status signal indicates whether the lighting is turned on or off.

The controller may be configured to turn on the lighting if the first signal indicates that the patient has exited the bed and the status signal indicates that the lighting is turned off. The controller may be configured to enable the lighting to remain turned on if the first signal indicates that the patient has exited the bed and the status signal indicates that the lighting is turned on. The controller may be configured to receive a second signal from the bed exit monitor and use the second signal to control the turning off of the lighting independently of the manually operated switch.

The bed exit monitor may be configured to detect a patient having entered the bed. The second signal may indicate that the patient has entered the bed. The controller may be configured to enable the lighting to turn off if the second signal indicates that the patient has entered the bed and the status signal indicates that the lighting has been turned off via the manually operated switch. The controller may be configured to generate an alert signal indicating whether the lighting is turned on or turned off in response to signals from the bed exit monitor.

The bed system may include an output device configured to display an indication of whether the lighting is turned on or turned off. The bed system may include an input device coupled to the controller, where the input device is configured to receive an input signal, and the controller is configured to use the input signal to enable or disable the turning on and turning off of the lighting in response to signals from the bed exit monitor independently of the manually operated switch. The bed system may include a connector coupled to the controller, where the connector is configured to couple the controller to a healthcare communication system.

The controller may be configured to send an alert signal to the healthcare communication system if the lighting is turned on or off in response to signals from an ambient light detector. The healthcare communication system may be a nurse call system.

According to another aspect of this disclosure, a room lighting control apparatus for use in connection with a room in which a bed usable by a patient is located, includes a controller configured to receive a position signal corresponding to the patient's position relative to the bed, use the position signal to determine whether to turn on lighting in the patient's room, the lighting being configured to provide illumination in the patient's room, and send a lighting control signal to the room lighting to turn on the room light if the patient has exited the bed. The controller may be configured to determine, from the position signal, whether the patient has exited the bed. The controller may be configured to determine whether the room lighting is turned on.

The room lighting control apparatus may include a detector coupled to the controller, wherein the controller is configured to receive a status signal from the detector, the status signal indicating whether the room lighting is turned on. The lighting control signal may be configured to enable the room lighting to remain turned on if the status signal indicates that the room lighting is turned on. The controller may be configured to receive a second position signal and send a second room lighting control to the room lighting to turn off the room lighting if the second position signal indicates that the patient is positioned on the bed.

According to another aspect of this disclosure, a room device control apparatus for use in connection with a room comprising a bed usable by a patient, where the room device control apparatus includes a controller configured to receive a position signal corresponding to the patient's position relative to the bed, use the position signal to determine whether to turn on a room device, the room device being configured to provide output in or adjacent to the patient's room, the room device being activatable by a manually operated switch, the controller being configured to send a room device control signal to the room device to turn the room device on or off in response to the patient changing position relative to the bed, independently of the manually operated switch, and a conduit coupling the controller to the room device. The conduit may include a wireless communication link.

BRIEF DESCRIPTION OF THE DRAWINGS

The detailed description particularly refers to the following figures, in which.

The same reference numbers may be used to refer to like components in the several drawings.

DETAILED DESCRIPTION

Figure 1:
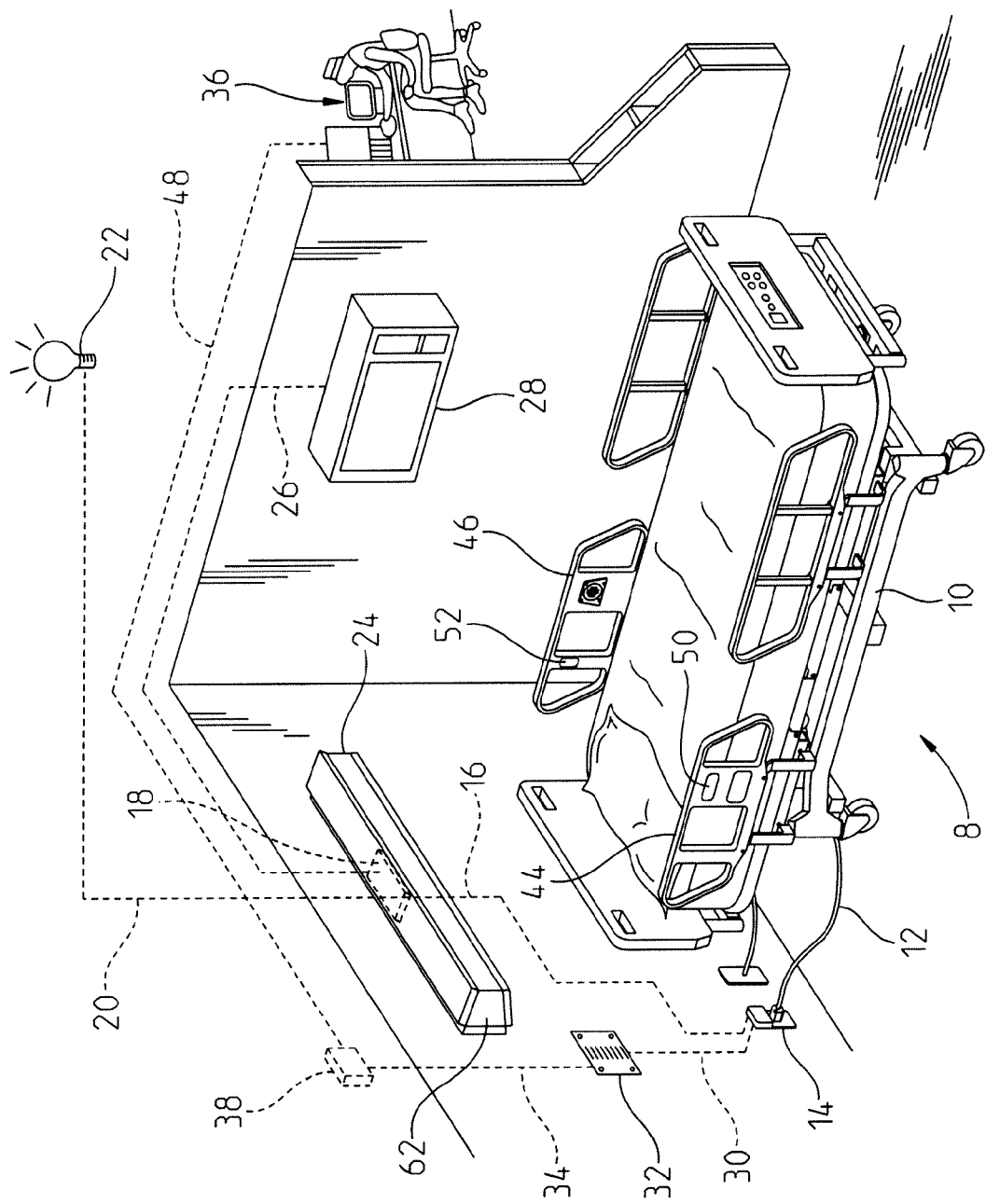
FIG. 1 is a perspective view of a patient's room, including a bed and a connection between the bed and room lighting.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, a patient's room 8 includes a bed 10 and one or more room devices, such as lighting 22, which may be located in the room 8 or an adjacent room, such as a washroom. Other possible room devices include an overbed light or night/reading light 24 and a television or entertainment system 28. The lighting 22, 24 may be coupled to the bed (e.g. to a portion of the bed frame, or to the headboard, foot board, or one of the siderails). Alternatively, the lighting 22, 24 may be spaced from the bed (e.g. mounted to a wall, table or ceiling of the room 8). In either instance, the lighting 22, 24 is configured to illuminate at least a portion of the room or an adjacent room (such as a washroom). In other words, the lighting 22, 24 is a device that provides ambient light upon being activated.

Typically, the bed 10 includes a frame supported by wheels or casters, a mattress supported by the frame, a number of siderails, a headboard and a footboard, as shown; however, all of these elements are not required for the purposes of the present disclosure.

The bed 10 has a number of electronically controlled functions. A patient input-output device 52 receives and processes electrical input (e.g. voltage) from number of manually operable switches (such as membrane switches or the like) coupled to the patient input-output device 52, which enable a patient to activate and deactivate certain bed functions when the patient is positioned on the bed 10. For example, some beds permit the patient to raise and lower the bed or certain sections thereof, place a call to a hospital communication system, such as a nurse call system, or turn on an overhead light, by touching these switches. The patient input-output device 52 includes circuitry configured to convey voltage generated by the manually operable switches to a bed controller 56, described below. In the illustrated embodiment, a patient input-output device 52 is mounted to the inwardly facing side of at least one of the siderails 44, 46 of the bed 10 (i.e., facing toward the mattress).

A caregiver input-output device 50 receives and processes electrical input (e.g. voltage) from one or more input devices mounted thereto, which enable a caregiver to configure, activate and/or deactivate certain of the electronically controlled bed functions. For example, some beds permit the caregiver to raise and lower the bed or certain sections thereof, or activate and deactivate other features of the frame or the mattress, such as chair, CPR, Trend, and reverse Trend positions, pressure relief, turn assist, or pulmonary therapy features of the mattress (e.g. lateral rotation, percussion and/or vibration features), by physically contacting the caregiver input-output device 50.

Figure 6:
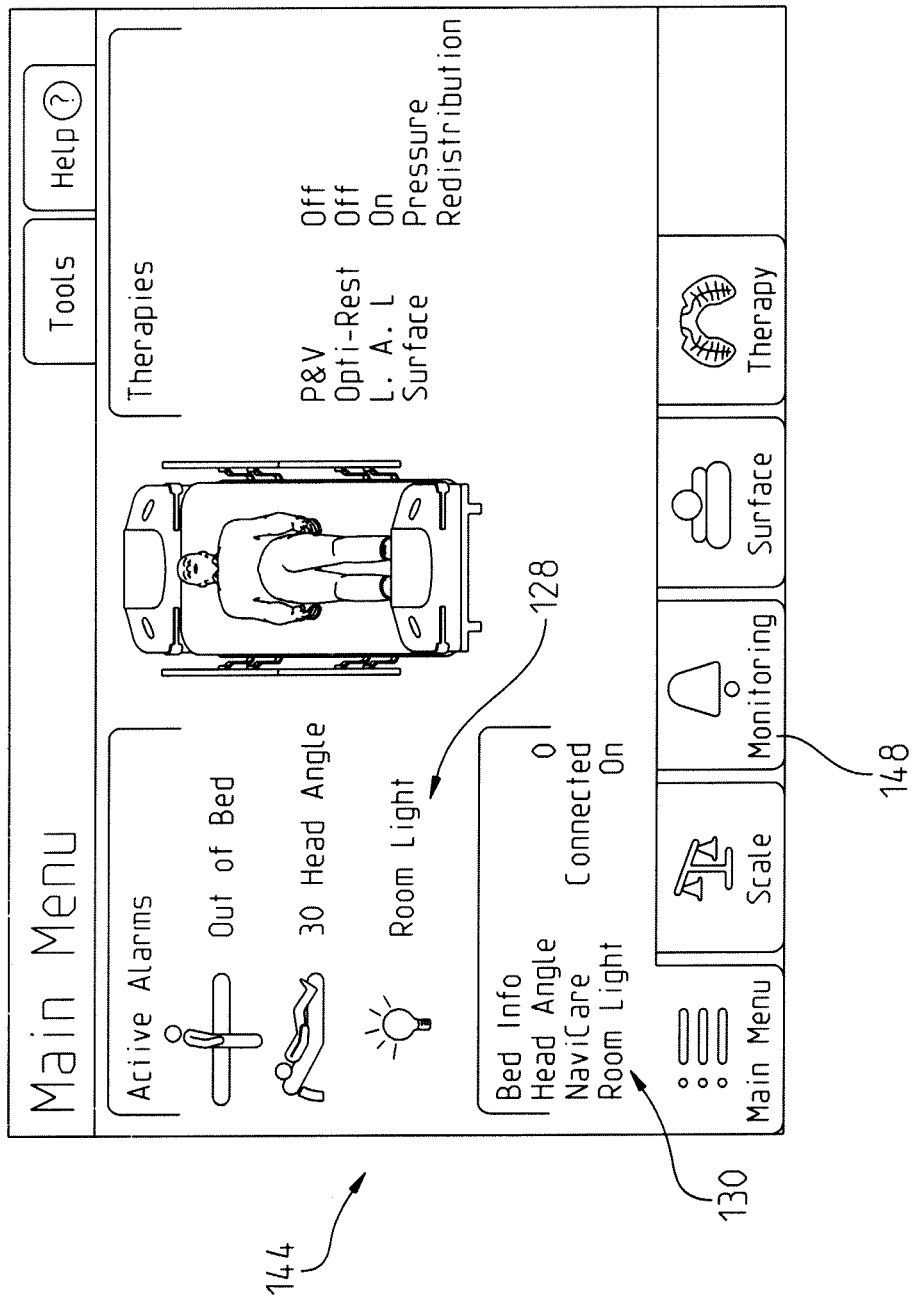
FIGS. 6-7 are sample screen displays for a bed system including a room lighting control feature.
Figure 7:
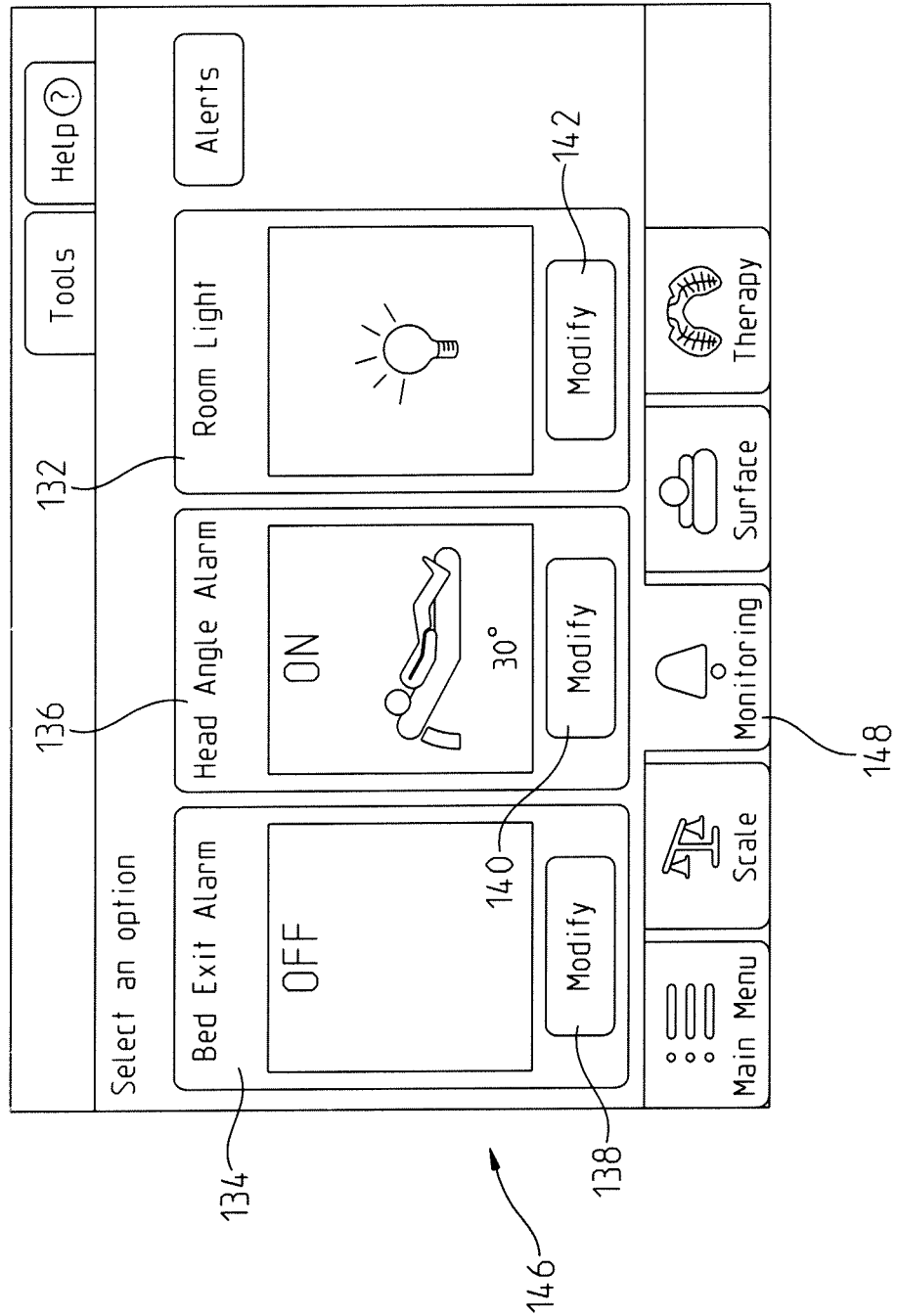

Typically, the caregiver input-output device 50 includes manually operable switches, such as membrane switches. Some caregiver input-output devices have touchscreen displays, which may include a graphical user interface. For example, FIGS. 6-7 illustrate touchscreen user interfaces that may be incorporated into the caregiver input-output device 50 to, among other things, enable a caregiver to configure, activate and/or deactivate the room lighting control features described herein. The caregiver input-output device 52 includes circuitry configured to convey voltage generated by the switches, touch sensors, or other input devices mounted thereto to the bed controller 56, described below. In the illustrated embodiment, a caregiver input-output device 50 is mounted to the outwardly facing side of at least one of the siderails 44, 46 of the bed 10 (i.e., facing away from the mattress).

A patient position monitor is coupled to the bed 10. In the illustrated embodiment, the patient position monitor includes a bed exit monitor 54. The bed exit monitor 54 includes one or more force sensors, or a weigh scale (not shown), and a controller, such as a microcontroller or microprocessor. The sensor or scale generates an electrical output (e.g. voltage) in response to a change in the patient's weight or a change in the force applied to the bed. The controller receives and processes the electrical output generated by the sensor or scale to determine whether a bed exit has occurred. If a bed exit has occurred, the controller generates an electrical output (e.g. voltage). The sensor or scale may be coupled to the bed frame, or may be supported by a pad, mat, or bladder that lies on top of, within, or underneath the mattress, for example.

The illustrated bed 10 has a built-in patient weighing system, similar to that of beds that are currently commercially available, such as the TotalCare® bed. The patient weighing system includes a weigh scale (e.g. a number of load cells) coupled to the frame, and a controller configured to determine the weight of a patient positioned on the bed based on the output of the weigh scale. In the illustrated embodiment, the patient weighing system also functions as a bed exit monitor. If the weight of the patient, as detected by the bed's built-in weighing system, decreases to zero or nearly zero in a short period of time (with a delay to account for patient movement in the bed), the bed considers this to be an indication that the patient has exited the bed. However, as noted above, there are many other forms of bed exit monitoring systems, including systems that do not involve the bed's weigh scale, systems that are incorporated into the mattress, and systems that are not attached to the frame or to the mattress, but rather are sold as separate devices that may be used in connection with the bed. The presently described room lighting control feature may be configured to receive and process bed exit signals from any bed exit monitoring device or system, whether or not the system is incorporated into the bed.

In some embodiments, the patient position monitor or bed exit monitor may be configured to detect other changes in the position of the patient relative to the bed, alternatively or in addition to bed exit. For example, some patient position monitors are capable of detecting when the patient is sitting up in bed, or sitting or laying on an edge of the bed. Other patient position monitors are capable of detecting the amount of movement, or lack thereof, of the patient over a period of time. Some beds that have a raisable head section have a monitor that is capable of monitoring the angle of the head section of the bed relative to the frame or relative to the horizontal (and thereby, the approximate angle of the patient's upper body). The presently described room lighting control feature may be configured to receive and process electrical output of a patient position monitor or bed monitor, whether the output relates to a bed exit or some other change in the position of the patient relative to the bed.

A conduit 12 conveys low voltage electronic communications generated by a patient position or bed monitor located at the bed 10 to one or more other devices that are spaced from the bed 10 (such as other devices that are in or adjacent to the room 8). The conduit 12 is coupled to a connector 14, which, as illustrated, is mounted to a wall of the room 8. In general, all or portions of the conduit 12, as well as other conduits mentioned in this disclosure (e.g. conduits 16, 20, 26, 30, 34, 48) may include direct connections or network connections facilitated using a suitable communications infrastructure and protocol (such as a Controller Area Network or Echelon network), and may include insulated wiring or cable, or may include a wireless transmitter that transmits the electrical signals wirelessly to a wireless transceiver using a suitable wireless communications protocol. The connector 14 may include a 37-D sub connector, a wireless transceiver, or an interface unit, such as an NIU (network interface unit), a BIU (bed interface unit), or other similar suitable electronic communications link.

A conduit 16, illustratively located in or behind a wall of the room 8, conveys the electronic communications from the connector 14 to a low voltage controller 18. The low voltage controller 18 converts the signals to the appropriate voltage needed for the receiving device. In the case of the lighting 22, the low voltage controller converts the low voltage received from the bed 10 to a high voltage (e.g. 120 VAC) suitable for illuminating the lighting 22.

In the illustrated embodiment, the low voltage controller 18 is located in a headwall 62; however, this need not be the case. The low voltage controller 18 may be mounted to, in, or behind a wall of the patient room 8. In some embodiments, the low voltage controller 18 may be located nearer to the room device(s) 22, 24, 28 to which it conveys high voltage than appears from the illustration of FIG. 1.

Electrical communications that originate at the bed 10 may also be communicated to a nurse call system or other healthcare communication system. In the illustrated embodiment, a conduit 30, illustratively located in or behind a wall of the room 8, conveys electrical signals that originated at the bed 10 from the connector 14 to a user station 32 of a nurse call system. The signals may then be conveyed by the user station 32 to a master station 36 of the nurse call system via a conduit 34, an input-output device 38 (e.g., a junction box or an input-output board), and a conduit 48. In other embodiments, the user station 32 may be omitted and the signals conveyed directly from the connector 14 to the input-output device 38 or to the master station 36. From the master station 36, the signals may be communicated to other components of the nurse call system (such as an electronic status board or a caregiver's mobile communication device) via an input-output board and/or a network switch, such as a power over Ethernet ("PoE") switch, server computers, networking equipment, and other electronic communications components as may be required to convey the electrical signals to the appropriate device or devices of the nurse call system.

Figure 2:
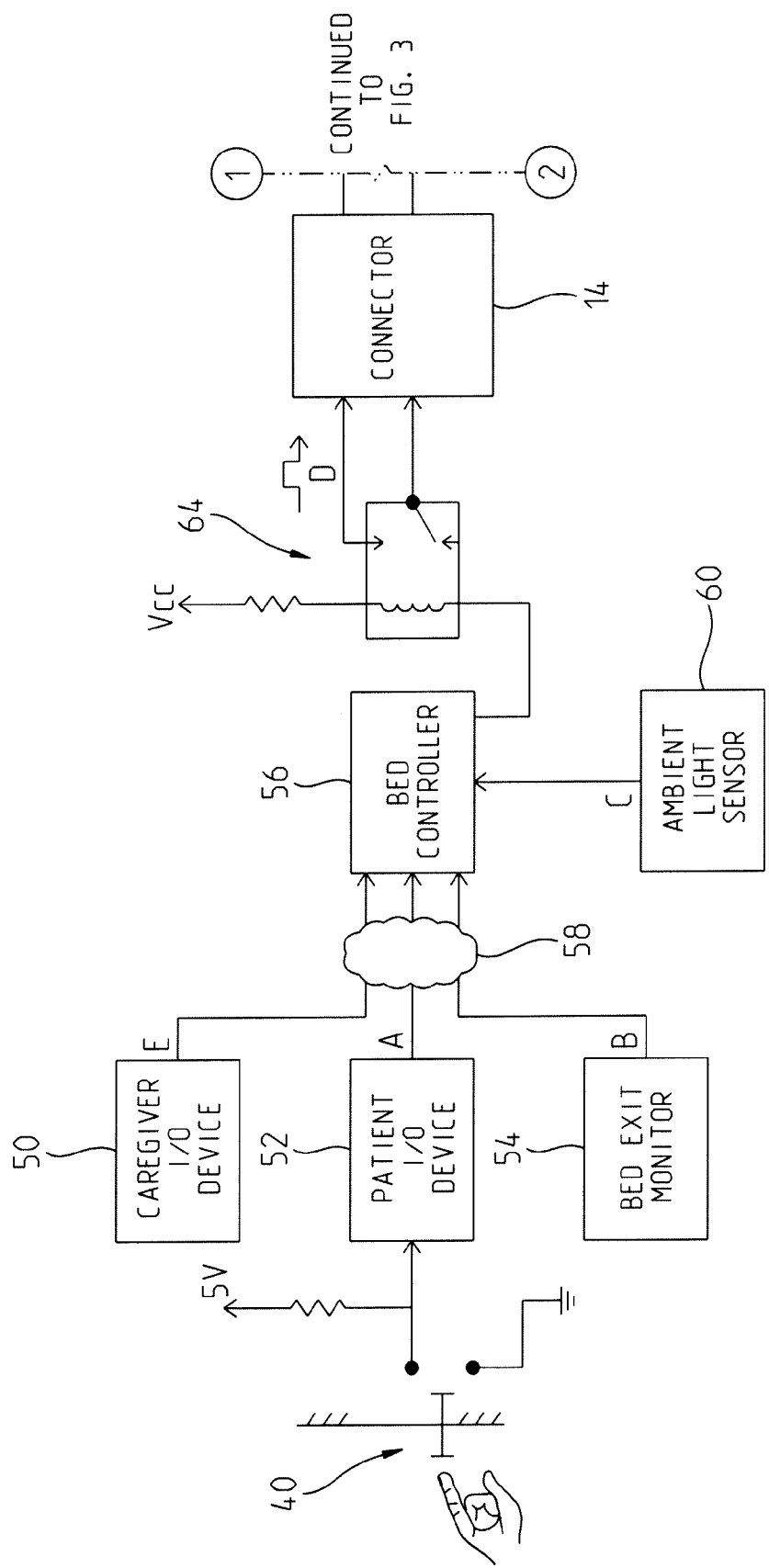
FIG. 2 is a schematic diagram illustrating a portion of one embodiment of a room lighting control system connected to a bed.

Referring to FIG. 2, electronically-controlled bed functions of the bed 10 are managed by the bed controller 56. The bed controller 56 includes one or more microprocessors or microcontrollers and electrical circuitry located in a housing that is mountable to a fixed location on the bed 10. In the illustrated embodiment, a bed controller 56 is located between the inwardly facing and outwardly facing sides of each of the siderails 44, 46, so that the patient input-output device 52 and the caregiver input-output device 50 are connected to opposite sides of the bed controller 56. However, the location of the bed controller 56 on the bed 10 is not important for the purposes of the present disclosure.

The bed controller 56 receives electrical input from other bed modules or devices via a bed network 58. The bed network 58 is an electronic network configured according to a CAN or Echelon protocol, or other suitable network communications protocol.

The designation "E" represents the occurrence of an event at the caregiver input-output device 50 in which a caregiver has turned on the room lighting control feature (e.g. by pressing a switch or activating a touchscreen control). If the event "E" occurs at the caregiver input-output device 50, a voltage output is transmitted to the bed controller 56 via the bed network 58. The bed controller 56 may store an indication that the event "E" has occurred in memory, which may be updated if the bed controller 56 receives an indication from the caregiver input-output device 50 that the room lighting control feature is turned off.

The lighting 22 or other room device (e.g. 24, 28) may be turned on by a manually operated switch 40. The designation "A" represents the occurrence of an event in which a person has contacted the manually operated switch 40 to turn on the lighting 22 or other room device. If the event "A" occurs, a voltage output is transmitted to the bed controller 56 via the bed network 58. In the illustrated embodiment, the manually operated switch 40 is located on the patient input-output device 52, which is mounted to a siderail 44, 46 of the bed 10. In other embodiments, the manually operated switch 40 may be a wall- or device-mounted switch for an overhead light located in the patient's room or an adjacent washroom, in which case, the switch 40 may be connected by suitable wiring to the bed controller 56 via the connector 14 and the conduit 12. If the switch 40 is a wall- or device-mounted switch, then, of course, the event "A" occurs at the switch 40 and not at the patient input-output device 52. The bed controller 56 may store an indication that the event "A" has occurred in memory, which may be updated if the bed controller 56 receives an indication from the patient input-output device 52 that the lighting 22 has been turned off.

The designation "B" represents the occurrence of an event at the bed exit monitor 54 in which a bed exit has been detected. If the event "B" occurs at the bed exit monitor 54, a voltage output is transmitted to the bed controller 56 via the bed network 58. The bed controller 56 may store an indication that the event "B" has occurred in memory, which may be updated if the bed controller 56 receives an indication from the bed exit monitor 54 that the patient has returned to the bed (e.g. by detecting at the bed exit monitor that a force has been applied to the bed).

The designation "C" represents the occurrence of an event in which ambient light is detected by an ambient light sensor or detector 60. The ambient light sensor 60 is located in an area that is illuminated when the lighting 22 is turned on. For example, if the lighting 22 is located in the patient's room, the ambient light sensor 60 is located in the patient's room. If the lighting 22 is located in an adjacent room (such as a washroom), then the ambient light sensor is located in the adjacent room. The ambient light sensor 60 may include a photodiode, phototransistor, or other suitable device for detecting ambient light. If the event "C" occurs at the ambient light sensor 60, a voltage output is transmitted to the bed controller 56.

The bed controller 56 includes circuitry configured to implement the logic: IF A OR [E AND (B AND NOT C)] THEN D. The designation "D" represents the occurrence of an event in which the result of executing this logic is "true." In other words, if the switch 40 has been touched, or the room lighting control feature is turned on and a bed exit has occurred and the lighting 22 is not on, then the event "D" has occurred. If the event "D" has occurred, then the bed controller 56 sends an electrical output in the form of a pulse to the connector 14 via a momentary relay 64.

Figure 3:
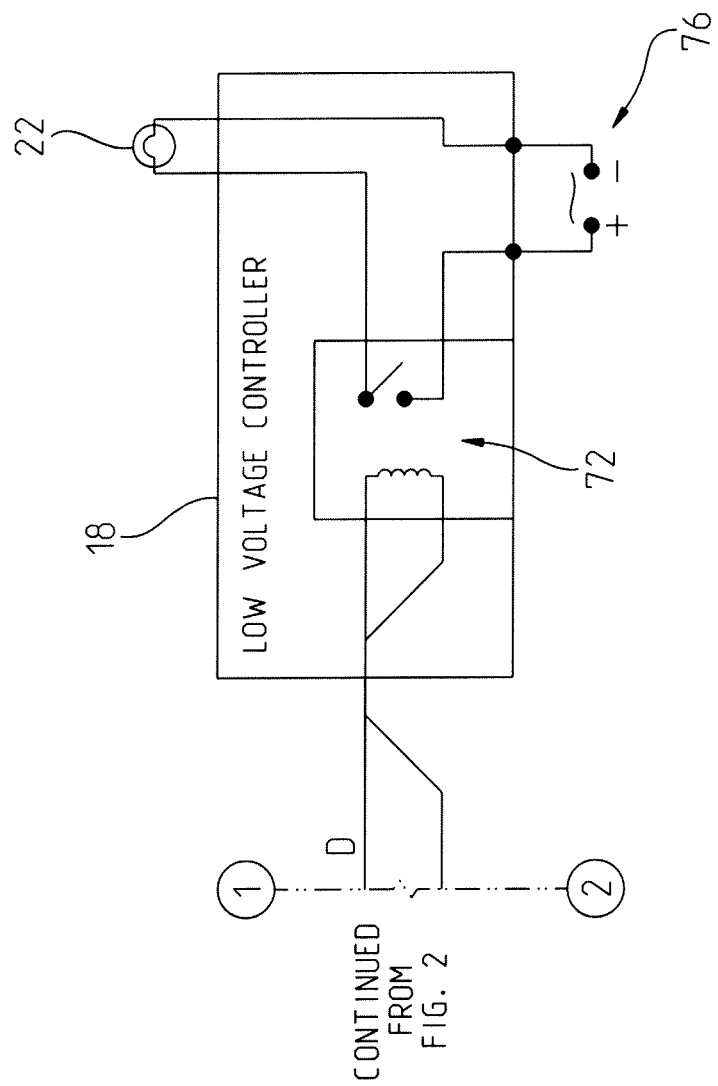
FIG. 3 is a schematic diagram illustrating another portion of the system of FIG. 2.

Referring to FIG. 3, the electrical output resulting from the occurrence of the event "D" is transmitted from the connector 14 to the low-voltage side of the low voltage controller 18 via the conduit 16. The low voltage controller 18 converts the low voltage to a high voltage via a high-voltage latching relay 72 coupled to a 120 VAC 76. The higher voltage then illuminates the lighting 22.

Figure 4:
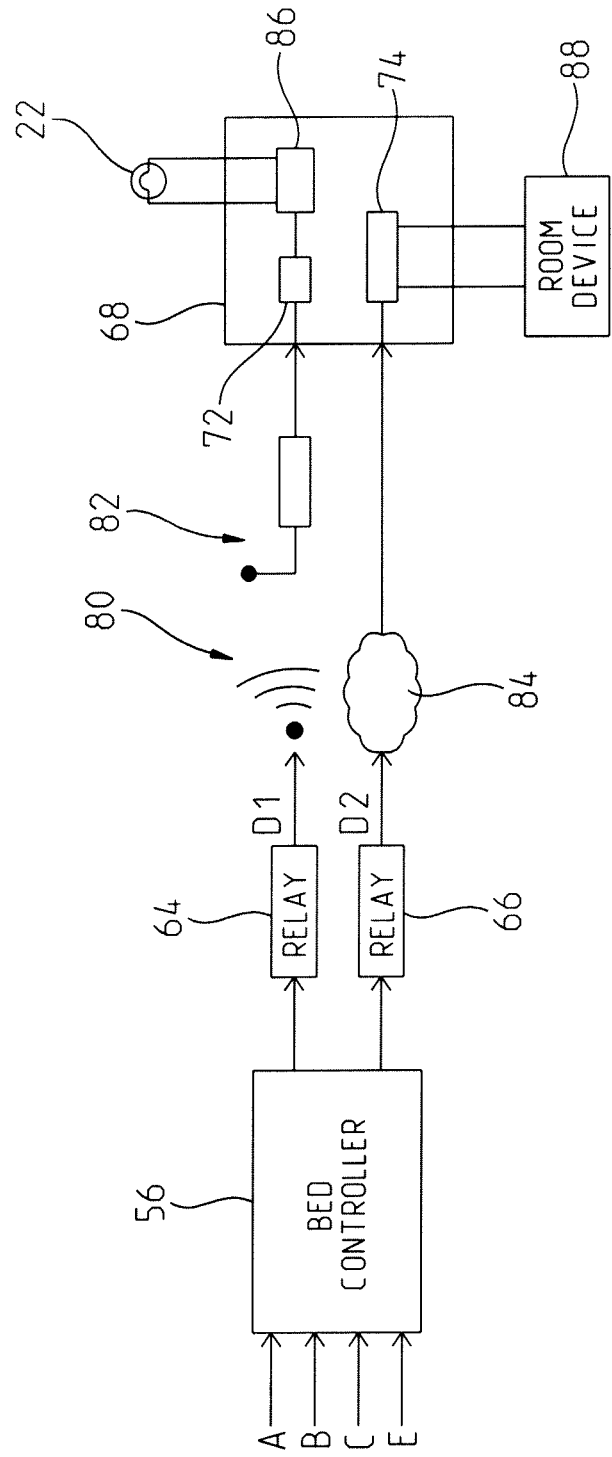
FIG. 4 is a schematic diagram illustrating another embodiment of a room lighting control system connected to a bed.

FIG. 4 illustrates another embodiment in which two room devices, the lighting 22 and another room device 88, are controlled by the room lighting control feature. The room device 88 may be the overbed light 24, the television or entertainment system 28, a room light or washroom light, or another device that is typically activated by a manually operated switch and is spaced from the bed 10.

In the embodiment of FIG. 4, the bed controller 56 receives electrical inputs in response to the occurrence of the events A, B, C, E, and executes the logic described above to determine whether the event "D" has occurred. If the event "D" has occurred, then the bed controller 56 transmits an electrical output (e.g. voltage) D1 to the lighting 22 and transmits an electrical output D2 (e.g. voltage) to the room device 88. The relay 66 is a momentary relay similar to the relay 64.

FIG. 4 additionally illustrates additional or alternative methods of communicating electrical output from the bed controller 56 to a low voltage controller 68. The low voltage controller 68 is similar to the low voltage controller 18 in many respects, however it contains additional components. The electrical output D1 is transmitted to the low voltage controller 68 via a wireless communication link including a wireless transmitter 80 and a wireless transceiver 82. The electrical output D2 is transmitted to the low voltage controller 68 via a communications network 84, which may be a CAN, Echelon, or other suitable network. In either case, the low voltage controller 68 may be modified to include additional circuitry to convert the received transmissions into a form that is usable by the circuitry of the low voltage controller 68.

Inside the alternate version of the low voltage controller 68 shown in FIG. 4, an additional high voltage latching relay 74 is used to convert the electrical transmission D2 to a higher voltage suitable for energizing the room device 88.

Also, the low voltage controller 68 includes a dimmer circuit 86, which is used to vary the intensity of the illumination when the lighting 22 is turned on. In this case, the low voltage controller 68 includes circuitry to implement the logic: IF A THEN FULL ON. In other words, if the event "A" occurs, then the lighting 22 is turned on at 100% intensity. The low voltage controller 68 also includes circuitry to implement the logic: IF [E AND (B AND NOT C)] THEN DIM. In other words, if the event "D" occurs, then the lighting is turned on at less than 100% intensity (e.g. at 50% of full intensity). The dimmer logic may be implemented using a microcontroller or with relays. If a microcontroller is used, then the dimmer circuit 86 may include a ramping feature whereby the intensity of the ambient light output by the lighting 22 is increased over a period of time in response to the occurrence of the event "D."

Figure 5:
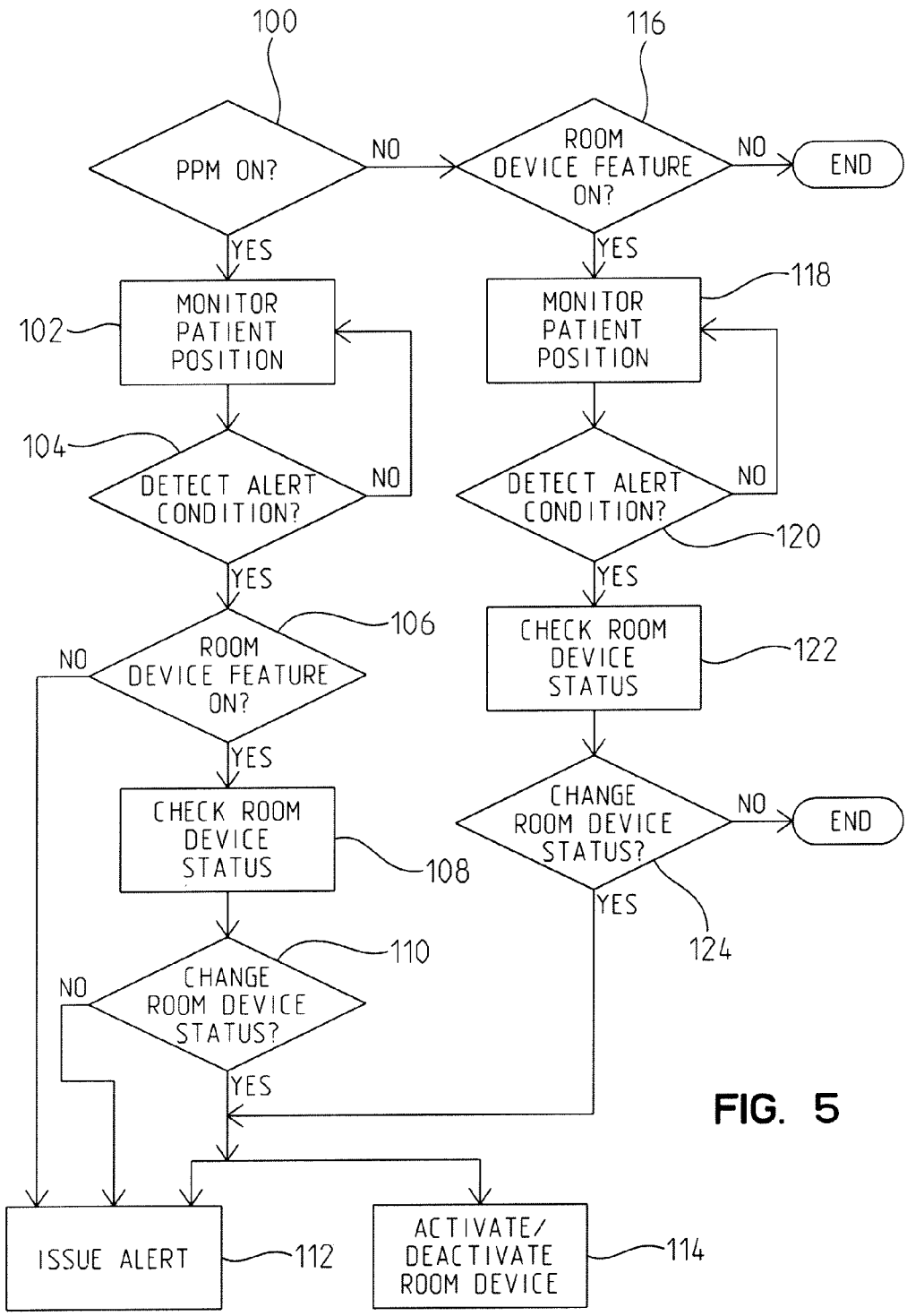
FIG. 5 is a flow diagram illustrating a process for controlling room lighting.

FIG. 5 illustrates a process that may be executed by the bed controller 56 to integrate the features of a room device control system (such as the room lighting control system described above) with a bed exit alarm system, and connect the room device control system to a nurse call system or other healthcare communication system. At step 100, the bed controller 56 determines whether a patient position monitor (e.g. the bed exit monitor 54) is turned on. If the patient position monitor has been turned on, then at step 102 the patient's position relative to the bed is monitored by the patient position monitor, for the occurrence of an alert condition, such as a patient exiting the bed, a patient entering the bed, or another change in position of the patient relative to the bed that may require a caregiver's attention.

At step 104, the bed controller 56 determines whether an alert condition has occurred (e.g., event "B"). If an alert condition has occurred, then at step 106, the bed controller 56 determines whether the room device control feature has been turned on (e.g., event "E"). If only the bed exit alarm is turned on, then the bed controller 56 issues a bed exit alert at step 112. The bed exit alert may include activating a visual indicator, such as a dome light, activating an audible alarm, and/or sending an electronic communication to an output device, such as a user station, master station, electronic status board, or mobile communication device connected to a nurse call system.

If the room device control feature is turned on, then at step 108 the bed controller 56 checks the status of the room device or devices that are connected to the room device control feature. For instance, in the case of the lighting 22, the bed controller 56 checks for the occurrence of the event "C." At step 110, the bed controller 56 determines whether the status of the room device needs to change. For instance, in the case of the lighting 22, if the event "C" has occurred, then the bed controller 56 proceeds to turn on the lighting 22 at step 114. However, if the lighting 22 is already turned on, then the status of the lighting 22 is not changed.

At step 112, the bed controller may send an alert indicating that the room device has been turned on, if the room device control feature of a particular installation has been configured to do so. Some versions of the room device control feature may not send any alerts, in which case the process may proceed directly to step 114. The bed exit alert may include activating a visual indicator, such as a dome light, activating an audible alarm, and/or sending an electronic communication to an output device, such as a user station, master station, electronic status board, or mobile communication device connected to a nurse call system.

At step 114, the bed controller 56 activates or deactivates the room device as needed according to the inputs and executed logic. For instance, if the room device control feature is configured to turn on a light in response to a patient exit, then the light is turned on at step 114. If the room device control feature is configured to turn off a light in response to a patient returning to his or her bed, then the light is turned off at step 114. There are many possible combinations of logic for turning a room device on or off in response to the detection of an alert condition relating to a patient's position relative to a bed, and any system that causes a room device to be activated or deactivated in response to the occurrence of such an alert condition falls within the scope of this disclosure.

The room device control feature may be used even if the patient position monitoring alarm (e.g. bed exit alarm) feature is not turned on. If the patient position monitor is not turned on, then at step 116 the bed controller 56 determines whether the room device control feature is turned on. If the room device control feature is turned on, then the bed controller 56 monitors the electrical output of the patient position monitor to determine at step 118. If the bed controller detects an alert condition at step 120, then at step 122 the bed controller 56 determines the status of the room device in a similar fashion as described above with reference to step 108. At step 124, the bed controller 56 determines whether the status of the room device needs to change in a similar fashion as described above with reference to step 110. If the status of the room device needs to change in response to the occurrence of the alert condition, then the process proceeds to step 112 (optional) and step 114, as described above.

The illustrated bed 10 includes a caregiver input output device 50 that may be configured to display a "main menu" user interface such as the user interface 144 shown in FIG. 6. The user interface 144 enables a caregiver to view the status of various bed features, including a room lighting control feature. The user interface 144 displays an indication 128 if the room lighting control feature is turned on. The user interface 144 also displays an indication 130 of the status of the room light. In the illustrated example, the user interface 144 indicates that the room lighting control feature is turned on and that the room light controlled by the room lighting control feature is turned on.

A user interface such as the user interface 146 shown in FIG. 7 is displayed if a caregiver contacts the monitoring button 148. The user interface 146 enables the caregiver to configure the bed exit alarm, head angle alarm, and/or room lighting control feature. If the bed exit alarm 134 is turned on (e.g. by a caregiver pressing the "modify" button 138, the bed 10 will send an alarm signal to the nurse call system if it detects the patient exiting the bed. Similarly, if the head angle alarm 136 is turned on (e.g. by a caregiver pressing the "modify" button 140), the bed 10 will send an alarm signal to the nurse call system if it detects the angle of the head section of the bed being lower than 30 degrees from horizontal.

As mentioned above, the room lighting control feature 132 can be turned on (e.g. by a caregiver pressing the "modify" button 142) independently of the bed exit alarm 134 and the head angle alarm 136. For example, if the bed exit alarm 134 is set, and the room lighting control feature 132 is turned on, and a bed exit is detected, the bed 10 will send a bed exit alarm signal to the nurse call system and turn on the room lighting (e.g. one or more of the room devices 22, 24, 28, as may be configured for a particular installation).

If the bed exit alarm 134 is not set, and the room lighting control feature 132 is turned on, and a bed exit is detected, the bed 10 will turn on the room lighting but will not send a bed exit alarm signal to the nurse call system. However, as described above, the bed 10 may send a room lighting signal to the nurse call system to indicate to the nurse call system that the room lighting has been turned on. If the room lighting control feature 132 is turned off, then the room lighting will not be controlled by the bed, but will instead be controlled by the manually operated switch 40.

There are many advantages of the present disclosure arising from the various features described herein. It will be noted that alternative embodiments of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A bed system, comprising
a bed,
a bed exit monitor coupled to the bed, the bed exit monitor being operable to detect a patient exiting the bed, and
a controller coupled to the bed exit monitor and to lighting configured to illuminate at least a portion of a room in response to being turned on, the lighting configured to be turned on by a manually operated switch, the controller being configured to receive a first signal from the bed exit monitor and use the first signal to control the turning on or off of the lighting independently of the manually operated switch, and to send an alert signal to a healthcare communication system if the lighting is turned on or off in response to signals from an ambient light detector.

2. The bed system of claim 1, comprising a detector coupled to the controller, the detector being configured to determine whether the lighting has been turned on or off via the manually operated switch, the controller being configured to receive a status signal from the detector, the status signal indicating whether the lighting is turned on or off.

3. The bed system of claim 2, wherein the controller is configured to turn on the lighting if the first signal indicates that the patient has exited the bed and the status signal indicates that the lighting is turned off.

4. The bed system of claim 3, wherein the controller is configured to enable the lighting to remain turned on if the first signal indicates that the patient has exited the bed and the status signal indicates that the lighting is turned on.

5. The bed system of claim 1, wherein the controller is configured to receive a second signal from the bed exit monitor and use the second signal to control the turning off of the lighting independently of the manually operated switch.

6. The bed system of claim 5, wherein the bed exit monitor is configured to detect a patient having entered the bed and the second signal indicates that the patient has entered the bed.

7. The bed system of claim 1, wherein the controller is configured to generate an alert signal indicating whether the lighting is turned on or turned off in response to signals from the bed exit monitor.

8. The bed system of claim 1, comprising an output device configured to display an indication of whether the lighting is turned on or turned off.

9. The bed system of claim 1, comprising an input device coupled to the controller, wherein the input device is configured to receive an input signal, and the controller is configured to use the input signal to enable or disable the turning on and turning off of the lighting in response to signals from the bed exit monitor independently of the manually operated switch.

10. The bed system of claim 1, comprising a connector coupled to the controller, wherein the connector is configured to couple the controller to a healthcare communication system.

11. The bed system of claim 10, wherein the controller is configured to send an alert signal to the healthcare communication system if the lighting is turned on or off in response to signals from an ambient light detector.

12. The bed system of claim 11, wherein the healthcare communication system is a nurse call system.

13. The bed system of claim 1, wherein the lighting is spaced from the bed.

14. The bed system of claim 1, wherein the lighting is coupled to the bed.

15. A bed system, comprising:
a bed,
a bed exit monitor coupled to the bed, the bed exit monitor being operable to detect a patient entering or exiting the bed,
an ambient light detector, and
a controller coupled to the bed exit monitor and to lighting configured to illuminate at least a portion of a room in response to being turned on and to be turned on by a manually operated switch, the controller being configured to:
receive a first signal from the bed exit monitor,
use the first signal to control the turning on or off of the lighting independently of the manually operated switch,
receive a second signal from the bed exit monitor, the second signal indicating whether the patient has entered the bed, and
use the second signal to control the turning off of the lighting independently of the manually operated switch,
receive a status signal from an ambient light detector, the status signal indicating whether the lighting is turned on or off, and
enable the lighting to turn off if the second signal indicates that the patient has entered the bed and the status signal indicates that the lighting has been turned off via the manually operated switch.

16. A room lighting control apparatus for use in connection with a room in which a bed usable by a patient is located, the room lighting control apparatus comprising:
a controller configured to receive a position signal corresponding to the patient's position relative to the bed, use the position signal to determine whether to turn on lighting in the patient's room, the lighting being configured to provide illumination in the patient's room, send a lighting control signal to the room lighting to turn on the room light if the patient has exited the bed, and send an alert signal to a healthcare communication system if the lighting is turned on or off in response to signals from an ambient light detector.

17. The room lighting control apparatus of claim 16, wherein the controller is configured to determine, from the position signal, whether the patient has exited the bed.

18. The room lighting control apparatus of claim 16, wherein the controller is configured to determine whether the room lighting is turned on.

19. The room lighting control apparatus of claim 18, comprising a detector coupled to the controller, wherein the controller is configured to receive a status signal from the detector, the status signal indicating whether the room lighting is turned on.

20. The room lighting control apparatus of claim 19, wherein the lighting control signal is configured to enable the room lighting to remain turned on if the status signal indicates that the room lighting is turned on.

21. The room lighting control apparatus of claim 16, wherein the controller is configured to receive a second position signal and send a second room lighting control signal to the room lighting to turn off the room lighting if the second position signal indicates that the patient is positioned on the bed.

22. A room device control apparatus for use in connection with a room comprising a bed usable by a patient, a first room device, and a second room device, the room device control apparatus comprising:
a controller configured to receive a position signal corresponding to the patient's position relative to the bed, use the position signal to determine whether to turn on at least one of the first room device and the second room device, the first and second room devices being configured to provide output in or adjacent to the patient's room, the first and second room devices each being activatable by a manually operated switch, the controller being configured to send a room device control signal to at least one of the first room device and the second room device to turn the at least one of the first room device and the second room device on or off in response to the patient changing position relative to the bed, independently of the manually operated switch, and send an alert signal to a healthcare communication system if the lighting is turned on or off in response to signals from an ambient light detector, and
a conduit coupling the controller to the first and second room devices.

23. The room device control apparatus of claim 22, wherein the conduit includes a wireless communication link.

* * * * *